United States Patent
Jung et al.

(10) Patent No.: US 9,024,274 B2
(45) Date of Patent: *May 5, 2015

(54) TARGETS FOR GENERATING IONS AND TREATMENT APPARATUSES INCLUDING THE TARGETS

(71) Applicant: Electronics and Telecommunications Research Institute, Daejeon (KR)

(72) Inventors: Moon Youn Jung, Daejeon (KR); Hyung Ju Park, Suwon (KR); Hyeon-Bong Pyo, Daejeon (KR); Nam Soo Myung, Seongnam (KR); Seunghwan Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/868,976

(22) Filed: Apr. 23, 2013

(65) Prior Publication Data

US 2013/0289331 A1    Oct. 31, 2013

(30) Foreign Application Priority Data

Apr. 25, 2012    (KR) .................. 10-2012-0043302

(51) Int. Cl.
| | |
|---|---|
| *G21K 5/04* | (2006.01) |
| *A61N 5/10* | (2006.01) |
| *H01J 27/02* | (2006.01) |
| *H01J 27/24* | (2006.01) |

(52) U.S. Cl.
CPC ............ *A61N 5/1077* (2013.01); *H01J 27/02* (2013.01); *A61N 2005/1088* (2013.01); *H01J 27/24* (2013.01)

(58) Field of Classification Search
CPC ............ H01J 3/04; H01J 3/14; H01J 27/00; H01J 27/02; H01J 27/022; H01J 27/16; H01J 27/26
USPC ................ 250/423 R, 424, 423 P, 423 F; 315/111.01, 111.21, 111.81
See application file for complete search history.

(56) References Cited

U.S. PATENT DOCUMENTS

2012/0153142 A1*   6/2012  Vertes et al. .................. 250/282

OTHER PUBLICATIONS ("Generation of fast ions by an efficient coupling of high power laser into snow nanotubes", Applied Physics Letters 91, 251501 (2007).*

* cited by examiner

Primary Examiner — Nicole Ippolito

(57) ABSTRACT

Provided are an ion generation target and a treatment apparatus including the target. The treatment apparatus includes a grid having a net shape of nano wires, an ion generation thin film attached to a side of the grid and generating ions by means of an incident laser beam, and a laser for emitting a laser beam into the nano wire of the grid to generate ions from the ion generation thin film and project the ions onto a tumor portion of a patient. The laser beam emitted into the nano wire forms a near field, the intensity of which is higher than that of the laser beam through a nanoplasmonics phenomenon, and the near field emits the ions from the ion generation thin film.

15 Claims, 4 Drawing Sheets

TARGETS FOR GENERATING IONS AND TREATMENT APPARATUSES INCLUDING THE TARGETS

CROSS-REFERENCE TO RELATED APPLICATIONS

This U.S. non-provisional patent application claims priority under 35 U.S.C. §119 of Korean Patent Application No. 10-2012-0043302, filed on Apr. 25, 2012, the entire contents of which are hereby incorporated by reference.

BACKGROUND OF THE INVENTION

The present invention disclosed herein relates to a target for generating ions and a treatment apparatus including the target, and more particularly, to a target for generating protons or carbon ions and an ion beam treatment apparatus including the target.

Methods for radiotherapy may include X-ray treatments, electron beam treatments, and ion beam treatments. Of these, the X-ray treatments are the lowest-cost treatment methods using the simplest device and are thus being most commonly used at the present day. Although it has been proven in 1950's that tumors can be treated by accelerating electrons using an accelerator to inject the electrons into the tumors, the electron beam treatments had not been taken over as one method for radiotherapy until electron accelerators were miniaturized in 1980's. In the X-ray treatments or the electron beam treatments, hydrogen bonds within cancer cells can be cut to destroy DNAs of the cancer cells. However, side effects in which healthy cells existing within the traveling path of X-rays or electron beams are seriously damaged may occur. Technologies such as intensity-modulated radiation therapy (IMRT), tomo therapy, and cyber knife have been developed as methods for reducing the radiation exposure of normal cells. However, the technologies cannot completely solve the above-described side effects.

The ion beam treatments are in the spotlight as treatment methods which can mitigate the side effects due to the X-ray treatments or the electron beam treatments. To allow the ion beam to penetrate a material, the ion beam should be accelerated to have high velocity, like the electrons. Even though the ion beam is gradually decreased in velocity when the ion beam penetrates a certain material, the ion beam is subject to the most energy loss of ionizing radiation just before the ion beam is stopped. This phenomenon is called a Bragg peak after William Henry Bragg, which discovered the phenomenon in 1903. Thus, in a case of such an ion beam treatment, malignant tumors may be selectively and locally treated when the ions are precisely controlled in velocity. When tumors are disposed at a deep position of the human body, protons or ions should be accelerated to a significantly high energy level at the outside of the human body. Methods of accelerating protons or ions may include a laser driven ion acceleration method. When high-power laser beam is emitted to a thin film, ions or protons within the thin film may escape with acceleration energy by a target normal sheath acceleration model (TNSA model) or a radiation pressure acceleration model (RPA model). After that, the ions may penetrate the body of a patient according to the acceleration energy to stop at a predetermined depth corresponding to the location of a tumor, and a large amount of free oxygen radicals may be generated at the predetermined depth to necrotize the tumor cells, which is a general principle of the ion beam treatment.

Ions, used in the ion beam treatment using the laser driven ion acceleration method, have the following two properties.

First, the ions should have high energy to arrive at a deep portion of a human body. Secondly, most of the ions should have substantially the same energy. Protons, having an energy level of about 250 MeV, can arrive at a portion located at a depth of about 20 cm in a human body. For example, ions having a high energy level of about 70 MeV may be used in a retinoblastoma treatment, and ions having a high energy level of about 200 MeV or higher may be used to treat a caner in a deep portion of a human body.

In addition, most of the protons or ions generated using a femtosecond laser should have uniform energy. Otherwise, ions may not be collected only in a tumor region. Accordingly, a normal tissue located out of the tumor region may be exposed to radiation.

In order to satisfy the two properties of ions, a target as an ion source should have a significantly small thickness. Thus, the target should be an ultra thin film.

In addition, a laser for accelerating the ions should have a significantly high energy of about $10^{19}$ to $10^{21}$ W/cm$^2$. This requires a significantly large laser system and high costs.

SUMMARY OF THE INVENTION

The present invention provides an ion generation target for generating protons or carbon ions of high energy, and an ion beam treatment apparatus including the ion generation target.

Embodiments of the present invention provide ion generation targets including; a grid having a net shape of nano wires; and an ion generation thin film attached to a side of the grid and generating ions by means of an incident laser beam.

In some embodiments, the ion may be a proton or a carbon ion.

In other embodiments, the ion may be the proton, and the ion generation thin film may be formed of a material including hydrogen.

In still other embodiments, the material including hydrogen may be a silicon nitride, a silicon oxide, or a metal.

In even other embodiments, the ion may be the carbon ion, and the ion generation thin film may include graphene.

In yet other embodiments, the grid may include silver, copper, gold, or aluminum.

In further embodiments, the grid may have a line width ranging from tens to hundreds nanometers.

In still further embodiments, the ion generation targets may further include a peripheral frame surrounding a periphery of the grid, wherein the ion generation thin film is attached to the peripheral frame.

In other embodiments of the present invention, ion beam treatment apparatuses include: the ion generation target; and a laser for emitting a laser beam into the nano wire of the grid to generate ions from the ion generation thin film and project the ions onto a tumor portion of a patient, wherein the laser beam emitted into the nano wire forms a near field, the intensity of which is higher than that of the laser beam through a nanoplasmonics phenomenon, and the near field emits the ions from the ion generation thin film.

In some embodiments, the grid may include silver, copper, gold, or aluminum.

In other embodiments, the grid may have a line width ranging from tens to hundreds nanometers.

In still other embodiments, the laser may be disposed at a side of the grid opposite to the ion generation thin film.

In even other embodiments, the laser beam may be a femtosecond laser beam.

In yet other embodiments, the laser beam may have a wavelength ranging from about 800 to 1,000 nanometers.

In further embodiments, the intensity of the near field may be tens to tens of thousands of times greater than that of the laser beam.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1A:
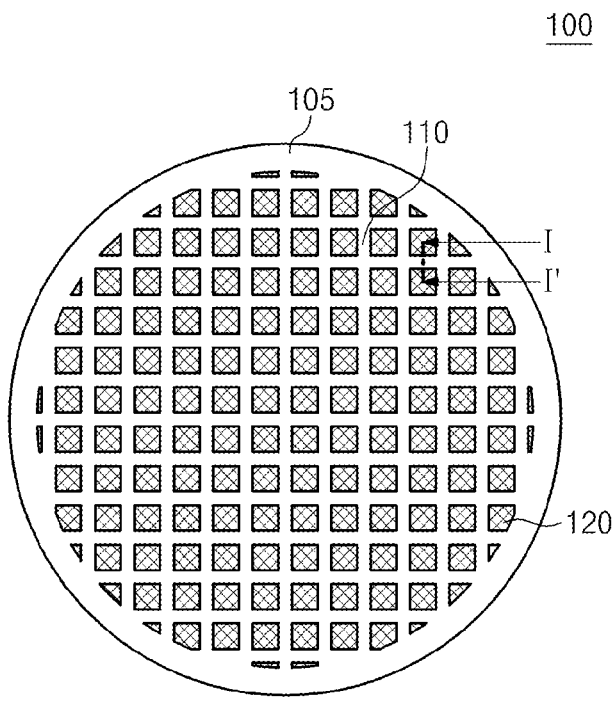
FIGS. 1A and 1B are a plan view and a side view, which illustrate an ion generation target used in an ion beam treatment apparatus according to an embodiment of the present invention.

Embodiments of the present invention will be described below in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Like reference numerals refer to like elements throughout.

In the following description, the technical terms are used only for explaining specific exemplary embodiments while not limiting the present invention. The terms of a singular form may include plural forms unless referred to the contrary. The meaning of 'comprises' and/or 'comprising' specifies a property, a region, a fixed number, a step, a process, an element and/or a component but does not exclude other properties, regions, fixed numbers, steps, processes, elements and/or components. Since exemplary embodiments are provided below, the order of the reference numerals given in the description is not limited thereto. In the specification, it will be understood that when a layer (or film) is referred to as being 'on' another layer or substrate, it can be directly on the other layer or substrate, or intervening layers may also be present.

Additionally, the embodiments in the detailed description may be described with cross-sectional views and/or plan views as ideal exemplary views of the present invention. In the figures, the dimensions of layers and regions are exaggerated for clarity of illustration. Accordingly, shapes of the exemplary views may be modified according to manufacturing techniques and/or allowable tolerances. Therefore, the embodiments of the present invention are not limited to the specific shape illustrated in the exemplary views, but may include other shapes that may be created according to manufacturing processes. For example, an etched region illustrated as a rectangle may have rounded or curved features. Thus, areas exemplified in the drawings have general properties, and are used to illustrate a specific shape of a device region. Accordingly, this should not be construed as limited to the scope of the present invention.

Figure 1B:
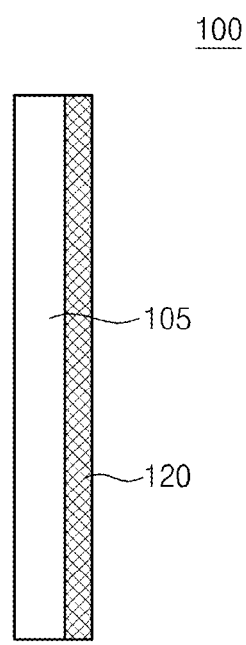

FIGS. 1A and 1B are a plan view and a side view, which illustrate an ion generation target used in an ion beam treatment apparatus according to an embodiment of the present invention.

Referring to FIGS. 1A and 1B, an ion generation target 100 includes a grid 110 having a net shape of nano wires, a peripheral frame 105 surrounding a periphery of the grid 110, and an ion generation thin film 120 attached to a side of the grid 110.

As illustrated in FIG. 1A as a plan view, the ion generation thin film 120 may be attached to the lower part of both the grid 110 and the peripheral frame 105 surrounding the grid 110.

The grid 110 may have a line width up to tens to several hundreds of nanometers. The grid 110 may include a material having significantly high electric conductivity. That is, the grid 110 may include silver (Ag), copper (Cu), gold (Au), or aluminum (Al). The shape of the grid 110 is the same as a net shape of a grid that is widely used in a transmission electron microscope (TEM) having a magnification of hundreds of thousands to observe an atomic layer of a material, but is different from the net shape in a line width of the grid 110 is significantly fine in a range of tens to hundreds nanometers.

Figure 2:
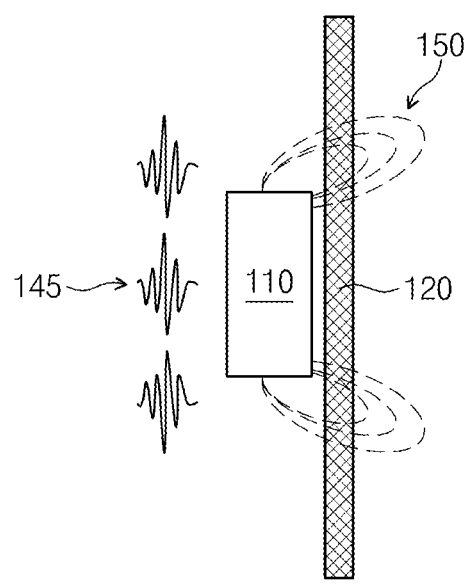
FIG. 2 is a cross-sectional view taken along line II' of FIG. 1A, which illustrates a phenomenon occurring at an ion generation target used in an ion beam treatment apparatus according to an embodiment of the present invention.

The peripheral frame 105 may support the grid 110 and delimit a region irradiated with a laser beam 145 (refer to FIG. 2). Also, the peripheral frame 105 may have a function to attach the ion generation thin film 120.

The ion generation thin film 120 may generate ions 210 (refer to FIG. 3) by means of an incident laser beam. The ions 210 may be protons or carbon ions.

When the ions 210 are protons, the ion generation thin film 120 may be formed of a material including hydrogen (H). The material including hydrogen may be a silicon nitride, a silicon oxide, or a metal. When the ions 210 are carbon ions, the ion generation thin film 120 may include graphene.

FIG. 2 is a cross-sectional view taken along line IT of FIG. 1A, which illustrates a phenomenon occurring at an ion generation target used in an ion beam treatment apparatus according to an embodiment of the present invention.

Referring to FIG. 2, when the laser beam 145 is incident to the grid 110 of the ion generation target 100 (refer to FIG. 1A), a nanoplasmonics phenomenon occurs at an edge of the grid 110 having a nanometer-sized line width. In the nanoplasmonics phenomenon, surface plasmon resonance in which light interacting with free electrons 160 (refer to FIG. 3) in a metal having a nanometer-sized line width is confined in a surface of the metal occurs, thereby increasing the intensity of an electromagnetic field at the surface of the metal. As such, when the laser beam 145 as light is incident to the grid 110 adapted for the nanoplasmonics phenomenon and having a nanometer-sized line width, surface plasmon resonance at the grid 110 generates a near field 150 as an electromagnetic field, the intensity of which is significantly high. The near field 150 transfers energy to the ion generation thin film 120 of the ion generation target 100 to generate the ions 210 (refer to FIG. 3) from the ion generation thin film 120. At this point, the intensity of the near field 150 may be tens to tens of thousands of times greater than the intensity of the incident laser beam 145.

Since a material having significantly high electric conductivity has a large number of free electrons therein, a material having significantly high electric conductivity is used to form the grid 110 of the ion generation target 100. That is, the intensity of the near field 150 generated by the surface plasmon resonance at the grid 110 can be further increased.

Figure 3:
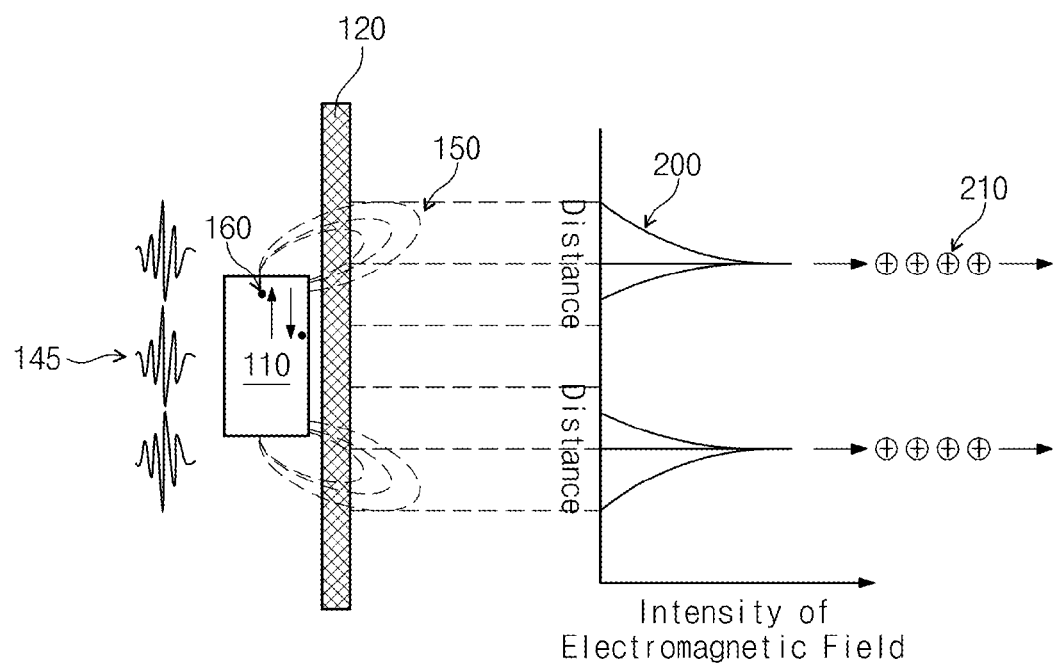
FIG. 3 is a schematic view illustrating that ions are accelerated by a phenomenon occurring at an ion generation target used in an ion beam treatment apparatus according to an embodiment of the present invention.

FIG. 3 is a schematic view illustrating that ions are accelerated by a phenomenon occurring at an ion generation target used in an ion beam treatment apparatus according to an embodiment of the present invention.

Referring to FIG. 3, the ions 210 may be emitted from the ion generation thin film 120 by the near field 150 generated through the nanoplasmonics phenomenon.

When the laser beam 145 is incident to the grid 110, the free electrons 160, the frequency of which matches the frequency of the laser beam 145, collectively move at the edge of the grid 110, particularly, undergo a resonance in which the free electrons 160 collectively move in a thickness direction at a side of the grid 110 as depicted with arrows (refer to the free electrons 160), thereby generating a surface wave. The generated surface wave generates the near field 150 as an intensive electromagnetic field in a significantly short distance (tens nanometers) from the edge of the grid 110. The intensive electromagnetic field is generated by accelerated motions of the free electrons 160.

An intensity 200 of the near field 150 is largest at a point where a resonance occurs, that is, at the edge of the grid 110. The intensity 200 of the near field 150 quickly decreases in a direction away from the edge of the grid 110. Such an intensity of the near field 150 may be tens to tens of thousands of times greater than the intensity of the laser beam 145 incident to the grid 110.

When the ion generation thin film 120 disposed at a side of the grid 110 of the ion generation target 100 (refer to FIG. 1A) is exposed to the near field 150, the intensity of which is tens to tens of thousands of times greater than the intensity of the incident laser beam 145, atoms contained in the ion generation thin film 120 are changed into the ions 210 through an ionization process and can be projected onto a tumor portion 340 (refer to FIG. 4) in a human body.

Figure 4:
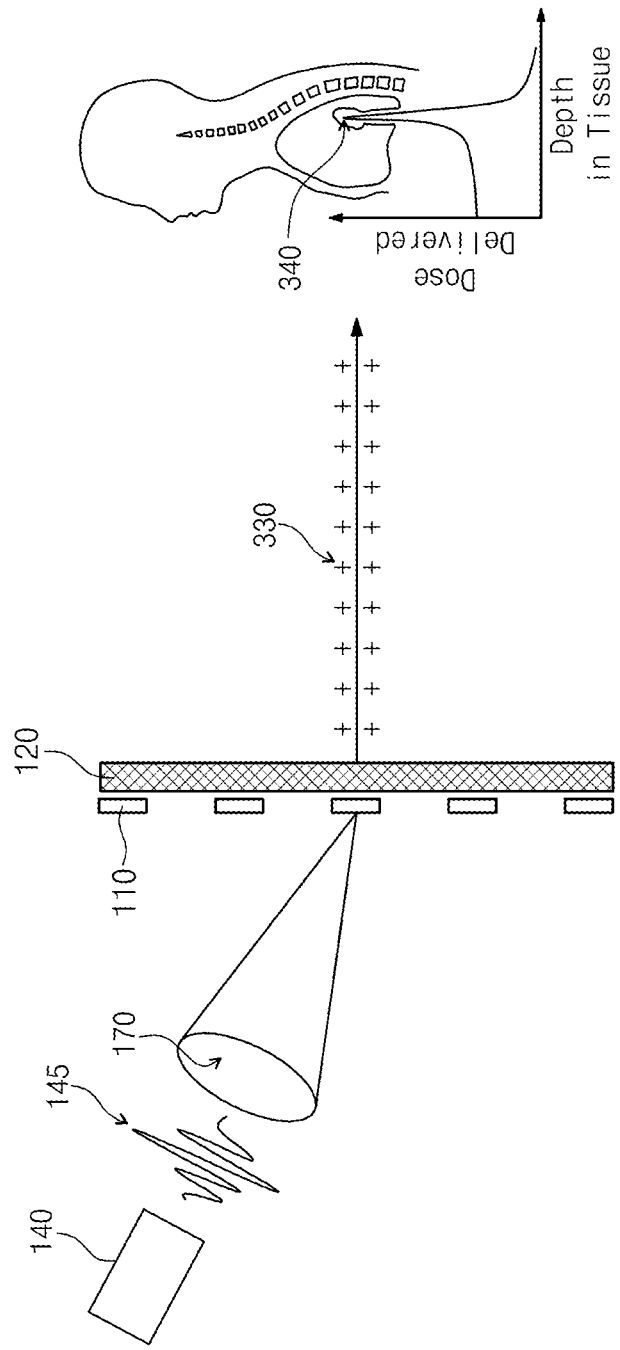
FIG. 4 is a schematic view illustrating an ion beam treatment apparatus according to an embodiment of the present invention.

FIG. 4 is a schematic view illustrating an ion beam treatment apparatus according to an embodiment of the present invention.

Referring to FIG. 4, an ion beam treatment apparatus includes a laser 140, an optical member 170, and an ion generation target (refer to reference number 100 of FIG. 1A).

The laser 140 may generate ions 330 from the ion generation target and project the ions 330 onto the tumor portion 340 of a patient. The laser 140 may emit the laser beam 145 to the ion generation target. The laser 140 may be disposed at a side of the grid 110 opposite to the ion generation thin film 120 of the ion generation target. The laser beam 145 may be a femtosecond laser beam. The laser beam 145 may have a wavelength ranging from about 800 to 1,000 nanometers. This is because the frequency of the laser beam 145 matches the frequency of free electrons of the grid 110 to cause a resonance, so that the free electrons can be accelerated.

The ion generation target may generate the ions 330 by receiving the laser beam 145 from the laser 140. The ion generation target may include the grid 110 having a net shape of metal wires having a nanometer-sized line width, and the ion generation thin film 120 disposed at a side of the grid 110.

The grid 110 may have a line width up to tens to hundreds of nanometers. The grid 110 may include a material having significantly high electric conductivity. That is, the grid 110 may include silver, copper, gold, or aluminum. The shape of the grid 110 is further same as a net shape of a grid that is widely used in a transmission electron microscope having a magnification of hundreds of thousands to observe an atomic layer of a material, but is different from the net shape in a line width of the grid 110 is significantly fine in a range of tens to hundreds nanometers.

The ion generation thin film 120 may generate the ions 330 by means of an incident laser beam. The ions 330 may be protons or carbon ions.

When the ions 330 are protons, the ion generation thin film 120 may be formed of a material including hydrogen. The material including hydrogen may be a silicon nitride, a silicon oxide, or a metal. When the ions 330 are carbon ions, the ion generation thin film 120 may include graphene.

The optical member 170 may focus the laser beam 145 on the grid 110. To this end, the optical member 170 may be an off-axis parabola mirror.

When the laser beam 145 is incident to the grid 110, surface plasmon resonance at the grid 110 generates the near field 150 (refer to FIG. 3), the intensity of which is higher than that of the laser beam 145. Thus, the ions 330 generated from the ion generation thin film 120 of the ion generation target may protons or carbon ions having high energy of tens to hundreds MeV. That is, the ions 330 generated from the ion generation thin film 120 of the ion generation target may have energy that is adjusted according to the intensity of a near field. Thus, the ions 330 can be stopped at the tumor portion 340 in the patient, and collide with the tumor portion 340.

When the femtosecond laser beam 155 is focused accurately on the grid 110, the ions 330 are accelerated by a near field generated at the edge of the grid 110 through the nanoplasmonics phenomenon.

The ions 330 may be set to be projected onto a position of the tumor portion 340 obtained from image diagnosis devices such as a magnetic resonance imaging (MRI) device, a computer tomography (CT) device, a positron emission tomography (PET) device, and an ultrasonic wave device, which are used for diagnosing the tumor portion 340 of the patient.

According to a treatment principle of the ion beam treatment apparatus, the laser beam 145 emitted from the laser 140 may be provided on the grid 110 of the ion generation target, and the ions 330 may be generated from the ion generation thin film 120 by a near field generated through surface plasmon resonance at the grid 110 and be projected into the body of a patient. Then, the ions 330 may be stopped at the tumor portion 340 located inside of the patient according to a Bragg peak principle, as illustrated in FIG. 4. At this point, the ions 330 may collide with the tumor portion 340 to generate free oxygen radicals, thereby disturbing tumor cells of the tumor portion 340.

That is, since the ions 330 collide with the tumor portion 340 to generate the free oxygen radicals, thereby disturbing the tumor cells of the tumor portion 340, the growth of the tumor cells may be thwarted or the tumor cells may be necrotized. Here, the disturbance of the tumor cells of the tumor portion 340 by the ions 330 may represent disturbance of DNA double helices of the tumor cells or disturbance of metabolic processes within nuclei of the tumor cells.

According to the generation and projection processes of the ions 330, when the laser beam 145 is incident into the grid 110 of the ion generation target, hydrogen atoms or carbon ions contained in the ion generation thin film 120 are changed to a plasma state in which the hydrogen atoms or carbon ions are divided into positive ions 330 and negative ions (not shown) by the energy of a near field generated through surface plasmon resonance at the grid 110. In this process, the negative ions further move away from the ion generation thin film 120 than the positive ions 330 to generate an electric field by a capacitor effect between the positive ions 330 and the negative ions. The positive ions 330 are accelerated toward the negative ions by the electric field so that each of the positive ions 330 has energy enough to be projected onto the tumor portion 340 located inside of the body of the patient from the outside of the body.

Since the accelerated positive ions 330 collide with the tumor portion 340 to generate the free oxygen radicals, thereby disturbing the tumor cells of the tumor portion 340, the growth of the tumor cells may be thwarted or the tumor cells may be necrotized. Therefore, the tumor portion 340 within the body of the patient may be treated.

According to the embodiments, since an ion generation target includes metal wires having a nanometer-sized line width, the intensity of a laser beam incident into the ion generation target can be increased. Thus, the ion generation target can generate protons or carbon ions of high energy without increasing the power of a laser.

In addition, since an ion beam treatment apparatus includes the ion generation target including metal wires having a nanometer-sized line width, protons or carbon ions of high energy can be projected onto a tumor portion in a patient. Thus, the ion beam treatment apparatus is adapted to economically treat a tumor portion in a patient.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An ion generation target comprising;
   a grid having a net shape of nano wires; and
   an ion generation thin film attached to a second side of the grid and generating ions using an incident laser beam directed at the first side of the grid,
   wherein the ion generation thin film comprises a first side adjacent to the side of the grid and a second side opposite to the first side, and
   wherein the ions are emitted from the second side of the ion generation thin film.

2. The ion generation target of claim 1, wherein the ion is a proton or a carbon ion.

3. The ion generation target of claim 2, wherein the ion is the proton, and the ion generation thin film is formed of a material comprising hydrogen.

4. The ion generation target of claim 3, wherein the material comprising hydrogen is a silicon nitride, a silicon oxide, or a metal.

5. The ion generation target of claim 2, wherein the ion is the carbon ion, and the ion generation thin film comprises graphene.

6. The ion generation target of claim 1, wherein the grid comprises silver, copper, gold, or aluminum.

7. The ion generation target of claim 1, wherein the grid has a line width ranging from tens to hundreds nanometers.

8. The ion generation target of claim 1, further comprising a peripheral frame surrounding a periphery of the grid,
   wherein the ion generation thin film is attached to the peripheral frame.

9. An ion beam treatment apparatus comprising:
   an ion generation target including a grid having a net shape of nano wires and an ion generation thin film attached to a second side of the grid and generating ions with an incident laser beam directed at the first side of the grid; and
   a laser for emitting a laser beam into the nano wire of the grid to generate ions from the ion generation thin film and project the ions onto a tumor portion of a patient,
   wherein the laser beam emitted into the nano wire forms a near field, the intensity of which is higher than that of the laser beam through a nanoplasmonics phenomenon, and
   the near field emits the ions from the ion generation thin film.

10. The ion beam treatment apparatus of claim 9, wherein the grid comprises silver, copper, gold, or aluminum.

11. The ion beam treatment apparatus of claim 9, wherein the grid has a line width ranging from tens to hundreds nanometers.

12. The ion beam treatment apparatus of claim 9, wherein the laser is disposed at a side of the grid opposite to the ion generation thin film.

13. The ion beam treatment apparatus of claim 9, wherein the laser beam is a femtosecond laser beam.

14. The ion beam treatment apparatus of claim 9, wherein the laser beam has a wavelength ranging from about 800 to 1,000 nanometers.

15. The ion beam treatment apparatus of claim 9, wherein the intensity of the near field is tens to tens of thousands of times greater than that of the laser beam.

* * * * *